(12) United States Patent
Smith

(10) Patent No.: US 11,376,036 B1
(45) Date of Patent: Jul. 5, 2022

(54) CIRCUMCISION DEVICE AND METHOD OF USE

(71) Applicant: PottyMD LLC, Knoxville, TN (US)

(72) Inventor: Dean Preston Smith, Knoxville, TN (US)

(73) Assignee: Wee Medical, LLC, Knoxville, TN (US)

(*) Notice: Subject to any disclaimer, the term of this patent is extended or adjusted under 35 U.S.C. 154(b) by 0 days.

(21) Appl. No.: 17/181,668

(22) Filed: Feb. 22, 2021

(51) Int. Cl.
*A61B 17/326* (2006.01)

(52) U.S. Cl.
CPC ................... *A61B 17/326* (2013.01)

(58) Field of Classification Search
CPC ..... A61B 17/326; A61B 17/282; A61B 17/00; A61B 17/12; A61B 2017/1225
See application file for complete search history.

(56) References Cited

U.S. PATENT DOCUMENTS

| 7,303,567 | B1 | 12/2007 | Smith | |
|---|---|---|---|---|
| 2007/0060928 | A1* | 3/2007 | Dave | A61B 17/326 606/118 |
| 2013/0090667 | A1* | 4/2013 | Dave | A61B 17/326 606/118 |
| 2018/0206876 | A1* | 7/2018 | Souaida | A61B 17/326 |

* cited by examiner

*Primary Examiner* — Tan-Uyen T Ho
*Assistant Examiner* — Bridget E. Rabaglia
(74) *Attorney, Agent, or Firm* — Baumgartner Patent Law; Marc Baumgartner

(57) ABSTRACT

Disclosed herein are circumcision devices, and methods of using the same, said devices having a protective cover over the glans after the device is placed onto the penis to protect during ligation, while also having a pull tab for more easily removing the protective cover after ligation. Furthermore, the devices disclosed herein can include a protective notch to prevent harm to the urethra and frenulum and a system to align the protective notch over the urethra and frenulum during placement of the device onto the penis.

18 Claims, 3 Drawing Sheets

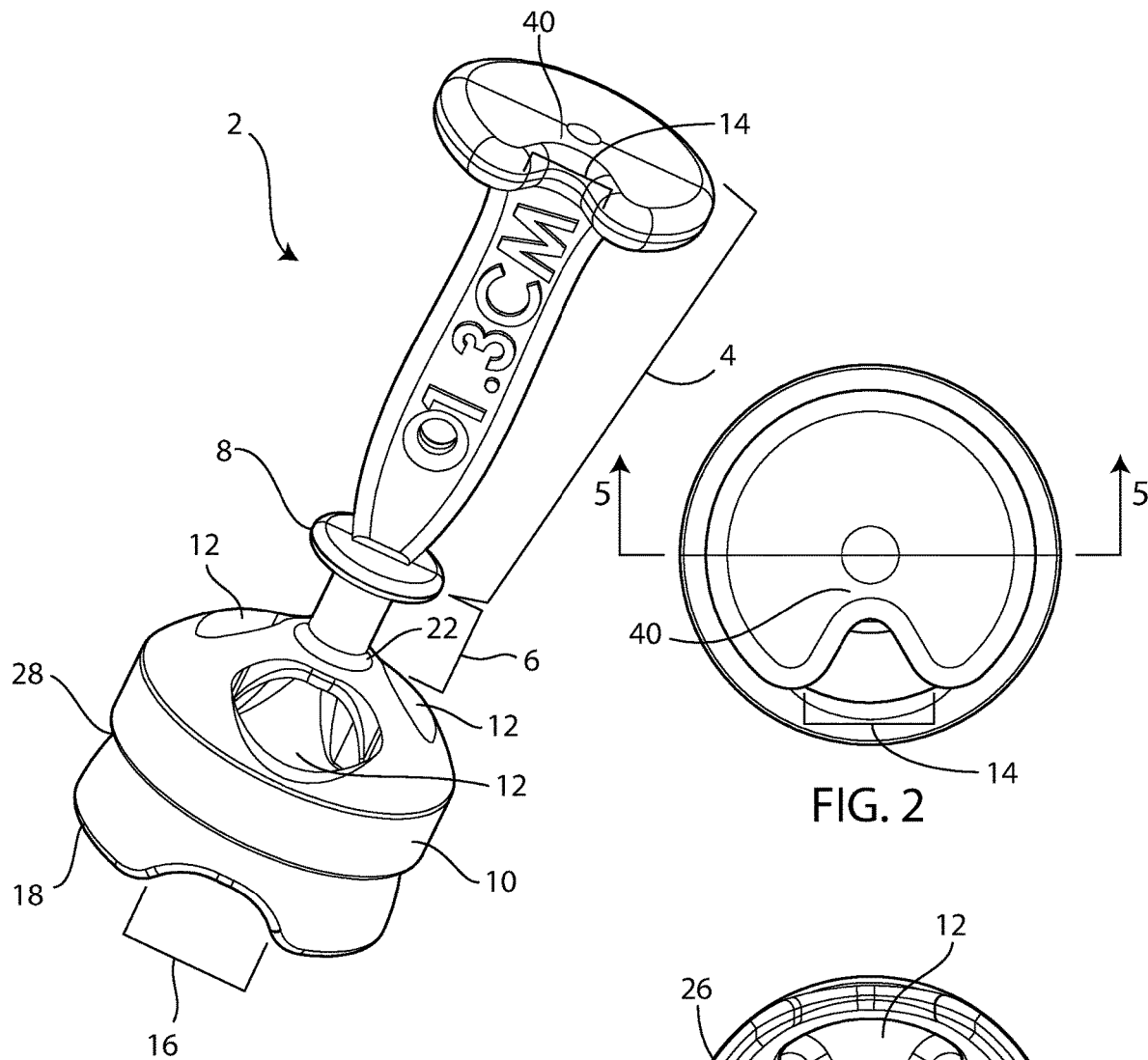
FIG. 1
FIG. 2
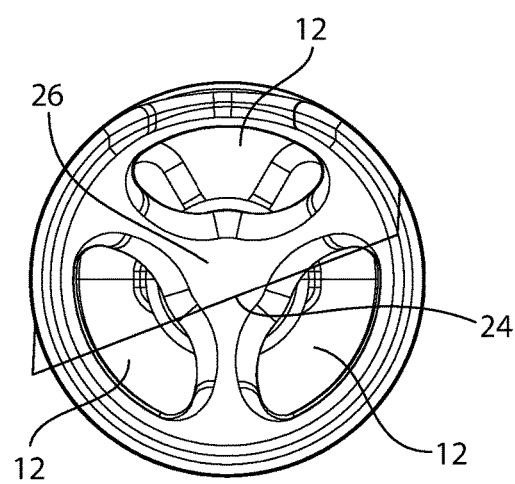
FIG. 3

CIRCUMCISION DEVICE AND METHOD OF USE

FIELD OF THE INVENTION

The invention pertains to the field of medical devices, more specifically a circumcision device and methods of using the same to remove foreskin from a penis.

BACKGROUND

Circumcisions have been performed for many years using a circumcision device having a tapered, bell-shaped ring adapted to fit over the glans of a penis and under the foreskin. The ring has an anterior end and a posterior end which is larger than the anterior end. A handle, integral with a bridge as connected to the anterior end, is grasped by the surgeon in properly positioning the ring over the glans. A string or ligature is subsequently tied around the foreskin so as to compress the foreskin into a groove that circumferentially extends around the exterior of the ring. The handle and bridge are then broken off and detached from the ring by means of a structurally weakened junction between the bridge and anterior end of the ring. After about 3-8 days, foreskin under and distal to the ligature dies, and the ring falls off the penis to complete the circumcision.

In some cases, after the circumcision device is positioned and prepared for circumcision with the ring received over the glans, factors such as body movement, penile erection, tissue changes, or simply a missized ring can cause the glans to slip partially or even entirely, through the ring and its smaller anterior end so as to excessively protrude therefrom and cause the ring to constrict the penis. As a result, the penis can swell and the ring may not fall off the penis after the normal period as intended. Possible resulting complications non-exclusively include strangulation or ischemia to the glans or distal penis, or damage to the urethra, as the ring can act like a tourniquet and constrict blood flow to the over-extended penis/glans. Failure of the ring to fall off the penis necessitates manual removal of the ring, which can require cutting the ring off the penis in an undesirable and delicate procedure.

To address the above-problems, U.S. Pat. No. 7,303,567 (The '567 patent) discloses a bridge having a handle fixedly, yet frangibly, attached to its anterior surface. The purpose being that the handle could be cleanly broken off the bridge after insertion of the ring onto the penis, thereby leaving the bridge on the penis during ligation to protect the glans during the 3-8 days it typically takes for the ring to fall off.

Despite the improvements disclosed in the '567 patent, further innovation is needed. Specifically, after ligation it is desirable for a practitioner to more easily remove the bridge/protective covering from the penis. This is difficult to do according to the teachings of the '567 patent because the handle is completely broken off from the bridge. Additionally, the frenulum and urethra are also vulnerable during circumcision and neither the '567 patent nor other prior art devices are sufficient in fully protecting these tissues during circumcision. Accordingly, there is a need in the art to protect the glans during the ligation period yet still offer a an easier way to remove a protective cover afterwards, while also adding additional protection for the urethra and frenulum.

SUMMARY

Preferred embodiments are directed to circumcision devices having a longitudinal axis having a protective cover having a posterior area and anterior area with an anterior surface, wherein the anterior area is fixedly attached to the proximal end of a pull tab that extends away from the anterior surface and terminates at a junction with a detachable handle, wherein the detachable handle comprises a distal end, and a proximal end that is fixedly, yet releasably attached to a distal end of the pull tab at the junction; and wherein the posterior area comprises an opening defined by a circumference configured to allow for the insertion of the penis glans into the protective cover.

Preferred devices have a pull tab between 2 mm to 2 cm in length. The distal end of the pull tab can have a wider circumference than the body of the pull tab. Preferably, the proximal end of the handle is frangibly attached to the distal end of the pull tab, and is configured to be detached through use of manual force. Advantageous embodiments encompass the pull tab being aligned along the longitudinal axis of the device.

Preferred embodiments include devices wherein the handle is aligned along the longitudinal axis of the device. Preferred devices can have a notch along the circumference of the posterior opening. Advantageously, the handle and/or pull tab can include an external indicator that is radially aligned with the notch. Preferably, the notch is between 3 to 14 mm long along the circumference of the posterior opening and is between 2 to 12 mm deep towards the anterior area. Advantageously, the anterior area of the of the protective cover is configured as having three bridges trisecting at the longitudinal axis to define three apertures.

Preferred methods of using the devices herein include positioning the glans of the penis through the posterior opening of the protective cover; ligating the foreskin around the protective cover; and detaching the handle from the pull tab.

Methods herein can include steps of pulling off the protective cover from the penis by grasping the pull tab and pulling away from the glans after the foreskin falls off from ligation. Preferably, the circumcision devices herein further comprise a notch along the circumference of the posterior opening and the handle and/or pull tab comprises an external indicator that is radially aligned with the notch; and wherein when positioning the protective cover over the glans, the notch is positioned over the frenulum and urethra by aligning the external indicator radially with the frenulum. It is preferred the practitioner removes the protective cover from the glans after ligation by pulling on the pull tab.

BRIEF DESCRIPTION OF THE FIGURES

FIG. 1 is a perspective view of a circumcision device.
FIG. 2 is an anterior view of the circumcision device.
FIG. 3 is a posterior view of the circumcision device.

DETAILED DESCRIPTION OF THE INVENTION

Figures 4, 5:
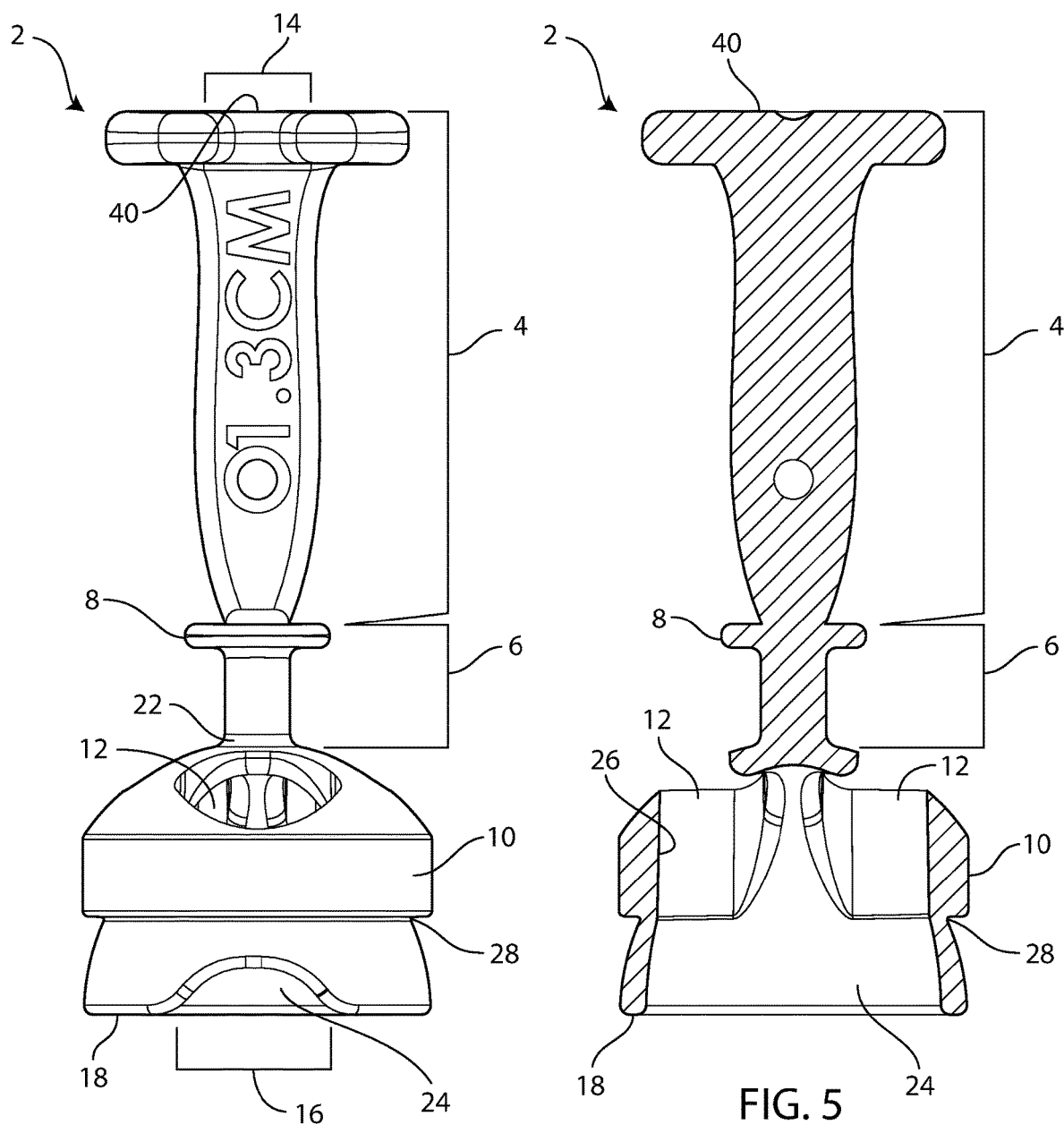
FIG. 4 is a side view of the circumcision device.
FIG. 5 is a cross-sectional side view of the circumcision device.

The present invention is directed to new circumcision devices, and methods of using the same, which are designed to avoid complications associated with prior art devices and methods.

According to preferred embodiments, and as shown in FIGS. 1-6, preferred circumcision devices 2 provided herein include a protective cover 10 having an anterior area 20 and a posterior area 18 along a longitudinal axis 42. The anterior area 20 includes a junction 22 where a pull tab 6 is fixedly attached and extends away from the anterior area 20 of the protective cover 10 along the longitudinal axis 42 and terminates at a junction 8 with a detachable handle 4, also aligned along the longitudinal axis 42, wherein the detachable handle 4 comprises a distal end 40, and a proximal end that is fixedly, yet detachable to a distal end of the pull tab 6 at the junction 8.

According to preferred embodiments, the handle 4 is releasably attached to the pull tab 6, such that it can be readily broken off after the protective cover 10 is correctly positioned on the glans 30. One preferred example of releasable attachment is through frangible attachment which can be achieved in a variety of ways but preferably involves the junction 8 being made of plastic. Non-exclusive frangible attachment can be achieved through plastic being thinner or otherwise more brittle or structurally weaker at the junction 8, compared to the remainder of the handle 4. Further ways for obtaining frangible attachment could include perforations and/or breaks at the junction 8. According to other embodiments the handle can be releasably attached to the pull tab, using non-frangible ways, including any suitable releasable attachment components, non-exclusively including hook and loop fasteners, snaps, clips, and tabs, for example. It is preferred that the practitioner can remove the handle 4 from the pull tab 6 using manual force, such as snapping, twisting, or pulling the handle off, but accordingly to non-preferred embodiments, the handle is cut away from the pull tab 6 using a cutting instrument such as scissors.

Figure 6:
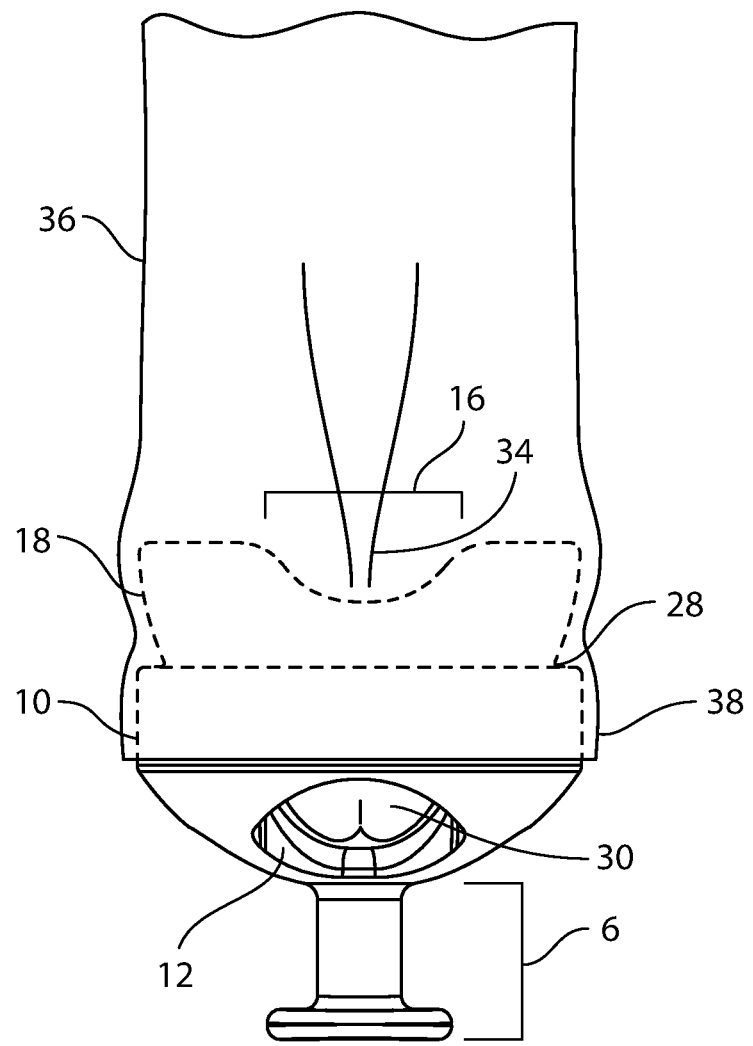
FIG. 6 is a view of the circumcision device with its handle detached and positioned on the penis during ligation.

After the handle 4 is detached at the junction 8, the pull tab 6 remains fixedly attached to the protective cover 10 at the junction 22 on the anterior area 20. The pull tab 6 is configured to allow the practitioner to remove the protective cover 10 from the glans 30 after ligation. The pull tab 6 is preferably between 2 mm-2 cm long from the junction 22 of the anterior area 20 and can have a distal end having a larger circumference than the body of the tab 6 for easier manipulation by the practitioner. FIG. 6 shows the pull tab 6 attached to the protective cover 10 after the handle 4 is broken off. The pull tab 6 preferably extends straight away from center of the anterior area 20, at the protective cover junction 22, and is also preferably aligned with the handle 4 along the longitudinal axis 42 of the device 2. According to non-preferred embodiments, the pull tab 6 and junction with the protective cover can be off center (not along the longitudinal axis 42) of the anterior area 20. Alternatively, the protective cover junction can be centered but the pull tab can be angled away from the longitudinal axis 42, such as in a slanted configuration.

The distal end 40 of the handle 4 can be any suitable configuration, yet preferably is like a pommel having a wider circumference than the remainder of the handle (e.g., shaft), as shown in FIG. 1. The wider circumference of the distal end 40 allows for easier manipulation of the device 2 by a practitioner, when positioning the coupled protective cover 10 onto the glans 30. As discussed in more detail below, the distal end 40 of the handle 4 can also include an external indicator 14 that is radially aligned with a notch 16 on the protective cover 10. A topside view of the distal end 40 of the handle and external indicator 14 is shown in FIG. 2.

The posterior area 18 of the protective cover 10 comprises a posterior opening 24 defined by a circumference configured to allow for the insertion of the glans 30 (head) of the penis 36 into the protective cover 10 prior to circumcision. Preferably, a multitude of devices 2 having different sized posterior openings 24 and protective covers 10 can be present in a kit, giving the practitioner a choice of which size to use depending on the size of the penis 36 and/or glans 30. In FIGS. 1 and 4 the length of the diameter (1.3 cm) of the posterior opening 24 is indicated on the device 2, on the handle 4. A preferred range of sizes can be between 1 and 1.7 cm in diameter, with 0.1 cm increments, for example. The sizing can be indicated on any portion of the device 2 or not shown at all. Color, shading, or other coding systems can be used to differentiate the protective cover sizes from each other. According to non-preferred embodiments, the device can have an adjustable posterior opening 24 allowing for smaller and larger circumferences of the posterior opening 24. A preferred range of sizes of the above-described embodiments can be between 1 and 1.7 cm in diameter, with 0.1 cm increments, for example.

As shown in FIG. 6, after insertion into the protective cover 10, the glans 30 is prevented from overextension and pinching by being contained within the inner surface 26 of the protective cover 10. According to a preferred embodiment, the anterior area 20 is configured as having three bridges trisecting at the longitudinal axis 42 to define three apertures 12. Having one or more apertures 12 is advantageous as it allows the wearer to urinate out of the protective cover 10. According to preferred embodiments one of the apertures is aligned with the notch 16 and the urethra 44 and configured to be large enough for urine to escape. The aligned aperture can have a larger opening than the other apertures, according to preferred embodiments. These apertures 12 are also useful for a practitioner to view the glans 30 during the procedure, and being openings, they allow circulation and access to the glans 30 such as in the rare situation where the practitioner needs to insert a catheter into the patient's bladder while the protective cover 10 is on the glans 30. These are advantageous features should a complication arise during the circumcision.

According to preferred embodiments, the apertures 12 are sized such that they are too small for the glans 30 to protrude out of. While shown in the drawings as a preferred trisecting structure, the anterior area 20 of the protective cover 10 can be any suitable shape configured to prevent overextension and pinching of the glans 30. Preferred covers are not completely solid, without any apertures. as it would not allow the release of urine from the patient. Alternative covers can comprise two bands that cross perpendicularly and define four apertures.

The protective cover 10 preferably includes a groove 28 that travels around the cover 10 circumferentially and is configured to receive ligature 32 positioned on top of the foreskin 38, as discussed below.

According to preferred embodiments, the posterior opening 24 includes a notch 16 along its circumference. The notch 16 is advantageous as it alleviates unwanted pressure and thus helps prevent pinching and damage to the frenulum 34 and the urethra 44 on the penis 36. Preferably the notch 16 is between 3 to 14 mm long (along the circumference of the posterior opening 24) and is between 2 to 12 mm deep (towards the anterior area 20). For these embodiments, it is also preferred to have an external indicator 14 positioned on the device 2 that is radially aligned with the notch 16 so that the practitioner can position the notch 16 over the frenulum 34 when the protective cover 10 is placed onto the glans 30. This embodiment is advantageous as it can be difficult to see the notch 16 during placement of the protective cover 10. More specifically, the aligned external indicator 14 can be easier to align with the frenulum 34 than the notch 16. As the external indicator 14 is already radially aligned with the notch 16, alignment of the external indicator 14 with the frenulum 34 ensures the notch 16 is also aligned and positioned over the frenulum 34.

While shown as a similar shaped notch positioned on the distal end 40 of the handle 4, the external indicator 14 can be any suitable marker and can be positioned in other locations on the device 2 so that it allows the practitioner to ascertain the position of the notch 16 along the circumference of the posterior opening 24. Non-exclusive examples of indicators can include a simple or geometric shape (e.g., circle, square, triangle), a protrusion, a nick, a color, and a drawings or icon. Other non-exclusive examples of locations the external indicator can be positioned that are radially aligned with the notch 16 include other areas of handle 4 (such as the shaft), the pull tab 6, and the anterior area 20 of the protective cover 10.

Preferably the entire circumcision device 2 is constructed out of the same material, more preferably medical grade plastic, such as transparent plastic for easy viewing. The device is preferably sterilized before use and can be embedded or coated with antibiotic/antiviral materials.

As shown in the bottom view of FIG. 3, the cross-sectional side view of FIG. 5, and the FIG. 6, the inner portion of the protective cover 10 is configured to receive the glans 30 of the patient and also prevent the glans 30 from undesirable protrusion out of the protective cover 10 by constraining it with the inner surface 26.

During circumcision of a penis, the foreskin 38 is typically pulled open with clamps, and a probe is inserted to tear the foreskin 38 off the glans 30. A "dorsal crush" is made to prevent bleeding, and a longitudinal slit is then cut in the foreskin 38. The foreskin 38 is laid back to expose the glans 30. The surgeon grasps the handle 4 of the circumcision device 2 and positions the protective cover 10 over the glans 30. For embodiments where the notch 16 is used, the practitioner can utilize the radially aligned external indicator 14 to position the notch 16 over the frenulum 34 to prevent undesired pressure in the area, including the urethra 44.

After the protective cover 10 is positioned on the glans 30, the foreskin 38 is pulled distally over the protective cover 10, followed by the tying of a ligature 32 around the foreskin 38 so as to compress the foreskin 38 into the previously described groove 28. The ligature 32 should have good tensile strength to avoid breakage, is preferably braided to avoid slipping or loosening when tying a knot, and can be coated or impregnated with an antibiotic to avoid infection. Excess foreskin 38 distal to the ligature 32 and adjacent to the anterior area 20 of the protective cover 10 can be trimmed off with scissors or scalpel. The handle 4 is detached from the pull tab 6, leaving the pull tab 6 connected to the anterior area 20 of the protective cover 10 at the junction 22. The penis 36 and the protective cover 10/pull tab 6 complex the at this point of the circumcision procedure is shown in FIG. 6.

During ligation, the practitioner, wearer, or parents can inspect the glans 30 through the apertures 12 or through transparent materials. After about 3-8 days, the protective cover 10/pull tab 6 complex falls off the penis 36 thereby removing foreskin 38 positioned distally from the ligature 32. After the foreskin 38 has fallen off, the practitioner can remove the protective cover 10 by grasping the pull tab 6 and pulling away from the glans 30.

The invention may be embodied in other specific forms besides and beyond those described herein. The foregoing embodiments are therefore to be considered in all respects illustrative rather than limiting, and the scope of the invention is defined and limited only by the appended claims and their equivalents, rather than by the foregoing description.

The invention claimed is:

1. A circumcision device having a longitudinal axis comprising:
    a protective cover having a posterior area and anterior area, wherein the anterior area is fixedly attached to the proximal end of a pull tab that extends away from the anterior area and terminates at a junction with a detachable handle, and wherein the distal end of the pull tab has a wider circumference than the body of the pull tab, and wherein the detachable handle comprises a distal end, and a proximal end that is fixedly, yet releasably attached to a distal end of the pull tab at the junction; and
    wherein the posterior area comprises an opening defined by a circumference configured to allow for the insertion of the penis glans into the protective cover.

2. The circumcision device of claim 1, wherein the pull tab is 2 mm to 2 cm in length.

3. The circumcision device of claim 1, wherein the proximal end of the handle is frangibly attached to the distal end of the pull tab, and is configured to be detached through use of manual force.

4. The circumcision device of claim 1, wherein the pull tab is aligned along the longitudinal axis of the device.

5. The circumcision device of claim 4, wherein the handle is aligned along the longitudinal axis of the device.

6. The circumcision device of claim 1, further comprising a notch along the circumference of the posterior opening.

7. The circumcision device of claim 6, wherein the handle and/or pull tab comprises an external indicator that is radially aligned with the notch.

8. The circumcision device of claim 7, wherein the notch is between 3 to 14 mm long along the circumference of the posterior opening and is between 2 to 12 mm deep towards the anterior area.

9. The circumcision device of claim 1, wherein the anterior area of the protective cover is configured as having three bridges trisecting at the longitudinal axis to define three apertures.

10. A method of circumcising the foreskin of a penis comprising:
    a protective cover having a posterior area and anterior area, wherein the anterior area is fixedly attached to the proximal end of a pull tab that extends away from the anterior area and terminates at a junction with a detachable handle, wherein the detachable handle comprises a distal end, and a proximal end that is fixedly, yet releasably attached to a distal end of the pull tab at the junction; and wherein the posterior area comprises an opening defined by a circumference configured to allow for the insertion of the penis glans into the protective cover;
    positioning the glans of the penis through the posterior opening of the protective cover;
    ligating the foreskin around the protective cover;
    detaching the handle from the pull tab; and
    pulling off the protective cover from the penis by grasping the pull tab and pulling away from the glans after the foreskin falls off from ligation.

11. The method of claim 10, wherein the circumcision device further comprises a notch along the circumference of the posterior opening and the handle and/or pull tab comprises an external indicator that is radially aligned with the notch; and wherein when positioning the protective cover over the glans, the notch is positioned over the frenulum and urethra by aligning the external indicator radially with the frenulum.

12. The method of claim 10, wherein the pull tab is 2 mm to 2 cm in length.

13. The method of claim 10, wherein the proximal end of the handle is frangibly attached to the distal end of the pull tab and is configured to be detached through use of manual force.

14. The method of claim 10, wherein the anterior area of the of the protective cover is configured as having three bridges trisecting at the longitudinal axis to define three apertures.

15. A method of circumcising the foreskin of a penis comprising:
   a protective cover having a posterior area and anterior area, wherein the anterior area is fixedly attached to the proximal end of a pull tab that extends away from the anterior area and terminates at a junction with a detachable handle, wherein the distal end of the pull tab has a wider circumference than the body of the pull tab, and wherein the detachable handle comprises a distal end, and a proximal end that is fixedly, yet releasably attached to a distal end of the pull tab at the junction; and wherein the posterior area comprises an opening defined by a circumference configured to allow for the insertion of the penis glans into the protective cover;
   positioning the glans of the penis through the posterior opening of the protective cover;
   ligating the foreskin around the protective cover; and
   detaching the handle from the pull tab.

16. The method of claim 15, wherein the circumcision device further comprises a notch along the circumference of the posterior opening and the handle and/or pull tab comprises an external indicator that is radially aligned with the notch; and wherein when positioning the protective cover over the glans, the notch is positioned over the frenulum and urethra by aligning the external indicator radially with the frenulum.

17. The method of claim 15, wherein the pull tab is 2 mm to 2 cm in length.

18. The method of claim 15, wherein the anterior area of the of the protective cover is configured as having three bridges trisecting at the longitudinal axis to define three apertures.

* * * * *